United States Patent [19]

Staeubli

[11] Patent Number: 4,570,898
[45] Date of Patent: Feb. 18, 1986

[54] CATHETER VALVE

[76] Inventor: Hugo Staeubli, Einsiedlerstrasse 240, 8810 Horgen, Switzerland

[21] Appl. No.: 475,291

[22] Filed: Mar. 14, 1983

[30] Foreign Application Priority Data

Mar. 12, 1982 [CH] Switzerland ............... 1593/82

[51] Int. Cl.$^4$ .......................................... F16L 55/14
[52] U.S. Cl. ............................. 251/4; 251/321; 604/250
[58] Field of Search ............... 604/250, 34; 251/4, 251/320, 321; 137/843

[56] References Cited

U.S. PATENT DOCUMENTS

| 3,100,486 | 8/1963 | Nehring | 251/4 X |
| 3,190,497 | 6/1965 | Anthon | 251/4 X |
| 3,191,600 | 6/1965 | Everett | 604/250 |
| 4,292,969 | 10/1981 | Raible et al. | 251/4 X |

Primary Examiner—Stephen C. Pellegrino
Attorney, Agent, or Firm—Craig & Burns

[57] ABSTRACT

A catheter and closure device in the form of a valve which remains in place at the hose during normal urination and has to be separated from the hose only for flushing out; the catheter valve includes a conical part serving for the insertion into the catheter hose; additionally, the valve includes on its inside a rubber-elastic valve hose adapted to be influenced from the outside, which during actuation of the valve is opened uninterruptedly but is closed in the non-actuated rest position by a single or multiple kink, fold or twist; the valve includes a fixed part with a through-bore as well as the rubber-elastic hose in extension of this bore; a sleeve with a spring 5 is placed over these parts, whereby the kinked hose is straightened out by the axial displacement of the sleeve opposite the spring force.

22 Claims, 5 Drawing Figures

CATHETER VALVE

The present invention relates to a catheter valve, especially with a part adapted to be plugged into the catheter hose.

It is customary heretofore to close off the catheter hose with the aid of a conical closure pin. This closure pin, used for decades, must be removed during each urination and subsequently be reintroduced into the hose end. Apart from the fact that the insertion of the pin is difficult by reason of the relatively small hose orifice and its possibly poorly accessible location, this is true in particular for older patients who frequently attempt in vain with shaky hands to place the pin correctly.

The present invention aims at providing a catheter end closure in the form of a valve which remains at the hose during normal urinating and has to be separated only for flushing out the hose end.

Such a catheter valve is also to reduce the infection danger and to improve generally the cleanliness since the undesired discharge of the urine is prevented.

A catheter valve of this type which fulfills the aforementioned requirements is characterized according to the present invention in that the catheter valve includes on its inside a rubber-elastic valve hose adapted to be influenced from the outside, which with an actuated valve is uninterruptedly open and in the non-actuated rest position is closed by single or multiple kinks, folds or twists.

These and other objects, features and advantages of the present invention will become more apparent from the following description when taken in connection with the accompanying drawings which shows, for purposes of illustration only, one embodiment in accordance with the present invention, and wherein.

Figure 1:
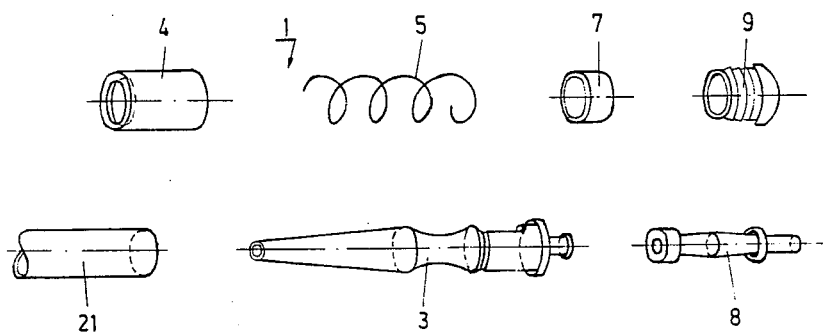
FIG. 1 is an exploded perspective view of a catheter valve in accordance with the present invention illustrating its individual parts.

Referring now to the drawing wherein like reference numerals are used throughout the various views to designate like parts, and more particularly to FIG. 1, the catheter valve 1 is composed of six parts; namely, of the valve nipple 3, of a sliding sleeve 4, of a coil spring 5 of stainless steel, of a spacer ring 7, of a buckling hose 8 as well as of a closure cap 9. Except for the parts 5 and 9, the remaining parts are preferably made from synthetic resinous material.

Figure 2:
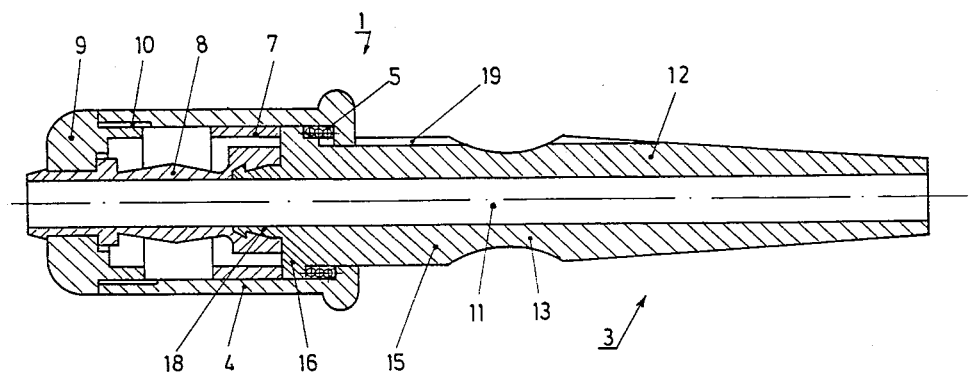
FIG. 2 is a longitudinal cross-sectional view through the catheter valve according to FIG. 1, in the open condition.

The catheter valve 1 is assembled in that the spring 5 is slipped over a conical pin portion 12 of the nipple 3 (FIG. 2), followed by the sliding sleeve 4. The buckling hose 8 is slipped over an extension 18 (FIG. 2) of the valve nipple 3 and subsequently the spacer ring 7 is placed over the buckling hose 8. Finally, the closure cap 9 is screwed together with the sliding sleeve 4 by means of its external thread 10, respectively, the internal thread 4 thereof under compression of the coil spring 5. The sliding sleeve 4 can now be released, whereupon the coil spring 5 presses the sleeve 4 toward the rear and thereby brings the buckling hose 8 into the triple kinked or folded position shown in FIG. 3. By sliding the sliding sleeve 4 forwardly, the buckling hose 8, i.e., the kinks or folds 30 thereof (FIG. 3) are straightened out, the passage is free and the valve is opened as shown in FIG. 2.

The spacer ring 7 prevents as to the rest an excessive compression of the buckling hose 8 which undoubtedly increases the length of its life.

Figure 4:
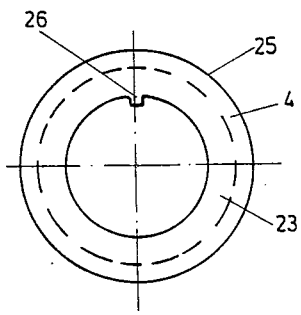
FIG. 4 is a rear elevational view of the sliding sleeve of the catheter valve in accordance with the present invention.

The valve nipple 3, i.e., the relatively fixed part of the valve 1, includes a continuous or uninterrupted through-bore 11. Its rear end is constructed as conical pin 12 (FIGS. 2 and 3) which is provided for the purpose to be inserted into the corresponding hose end 21 (FIG. 1) of a catheter hose. The conical pin 12 is followed by a support portion 13, which serves as abutment for the actuating thumb when pushing the sliding sleeve 4 forwardly. A spring-guide cylinder 15 for guiding the coil spring 5 follows the support portion 13. A guide disk 16 for the guidance of the sliding sleeve 4 is provided at the end of the guide cylinder 15. The guide disk 16 serves also as spring plate for the fixed end of the coil spring 5. An extension 18 follows the disk 16, which serves for the mounting of the one end of the buckling hose 8. The valve nipple 3 is additionally provided with a groove 19, in which slides a guide cam 26 (FIG. 4) of the sliding sleeve 4 for the purpose of preventing a rotation of the sliding sleeve 4 and therewith a more difficult actuation during the opening of the valve.

The sliding sleeve 4 includes a collar 23 (FIG. 3) which serves as spring plate for the displaceable end of the coil spring 5. A handle bulge 25 permits an improved support of the thumb during forward displacement of the sliding sleeve 4 for purposes of opening the valve.

Figure 5:
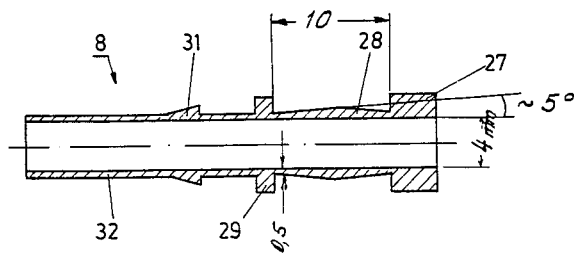
FIG. 5 is a longitudinal cross-sectional view through the buckling hose of the catheter valve in accordance with the present invention.

As shown in FIG. 5, the construction of the buckling hose 8 is quite complicated with a view toward its closure function. It includes a retaining bead 27 which is placed over the extension 18 of the valve nipple 3. It is adjoined by the buckling part 28, properly speaking, which with constant passage initially increases conically in order to decrease again beginning from the center and correspondingly up to its abutment bead 29. A further cylindrical part is followed by a retaining collar 31 which is supported on the closure cap 9 from the outside.

Figure 3:
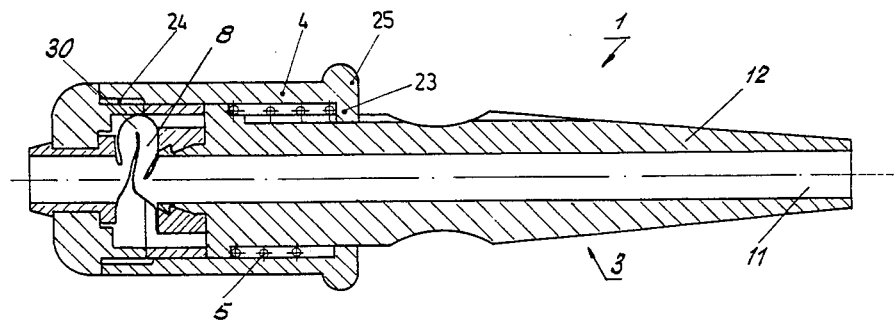
FIG. 3 is a longitudinal cross-sectional view, similar to FIG. 2, through the valve in the closed condition.

The buckling hose 8 terminates in a hose orifice part 32 which projects beyond the closure cap 9. However, it is also possible as shown in FIGS. 2 and 3, to omit the hose orifice part 32. This offers the advantage of reduced bulkiness during caring of the valve in the clothing but entails the disadvantage of the probable wetting of the remaining valve parts by urine.

The critical part of this valve made according to the type of construction of a squeeze valve is undoubtedly the buckling hose 8 which can be seen in its details in FIG. 5. The conicity of double-cone-shaped buckling part 28, properly speaking, amounts to about 5°, i.e., the entire opening angle of the cone is about 10°. With a through-passage of 4 mm. and a minimum wall thickness of 0.5 mm. at the transition places of the buckling part 28 into the retaining bead 27 and the abutment bead 29, the buckling length amounts to about 10 mm. It should be noted in that connection that during the forward sliding of the sliding sleeve 4, i.e., during the opening of the valve 1, the hose 8 is able to move preferably by its own forces out of the triple kinked position according to FIG. 3 into the stretched position according to FIG. 2. At any rate, even with a fatigued hose 8, this movement is positively assured thereby by the retaining collar 31, at which the sleeve 4 takes along the buckling hose 8 during forward displacement.

With this specific configuration of the buckling hose 8, a triple folding or buckling and therewith a quite secure closing of the hose, respectively, closing of the valve 1 is achieved.

The valve 1 is actuated either by the use of both hands or single-handed by means of the thumb. It has to be displaced forwardly and retained for such length of time until all of the urine has discharged.

Since it is possible is principle to close a hose not only by single or multiple kinks but also be a rotary movement or by a combined rotary sliding movement, the described sliding sleeve can also be constructed in principle as axially fixed rotary sleeve or as so-called rotary slide member having a combined rotary and longitudinal movement. In this case, the hose would have to be connected with the element constructed in that case as sleeve—it is also possible to provide an inner sleeve movable from the outside by means of a pin—in order to transmit to the hose the necessary rotary and/or sliding movement in the axial direction. If a pure twisting is provided, then in lieu of a torsion spring also a torsion rod may be provided.

The valve according to the present invention, in addition to the already indicated advantages, further offers the advantage that it cannot be lost as with the hitherto-used pins, and in that quite generally it is an agreeable auxiliary means for both patient and caring personnel in case of a permanent catheter.

Since the valve has no sharp edges and corners and no hard projecting parts, the danger of getting stuck at clothing pieces is extraordinarily slight.

The hose 8 is kept in the extended position during storage by means of a securing pin, adapted to be plugged-in into the fixed part 3 at the rear edge of the sleeve 4 with an open valve (FIG. 2), which prevents buckling or kinking damages.

While I have shown and described only one embodiment in accordance with the present invention, it is understood that the same is not limited thereto but is susceptible of numerous changes and modifications as known to those skilled in the art, and I therefore do not wish to be limited to the details shown and described herein but intend to cover all such changes and modifications as are encompassed by the scope of the appended claims.

I claim:

1. A normally closed catheter valve operable to be opened by actuation thereof, comprising a relatively fixed part with a through-flow bore, a rubber elastic valve hose means on the inside of the valve and adjoining the relatively fixed part substantially in extension of said bore, said valve hose means being closed in the non-actuated normal position of the valve by deformation of the hose means and being continuously open while the valve is actuated, a spring-loaded element, a spring operatively connected with said spring-loaded element, said spring-loaded element being operatively associated with said valve hose means and being movable relative to the relatively fixed part and operable by its movement in a direction opposite the spring force to open the closed hose means.

2. A catheter valve according to claim 1, characterized in that said spring-loaded element is a sleeve adapted to be placed over said relatively fixed part.

3. A catheter valve according to claim 2, characterized in that the sleeve is a rotary sleeve and the spring a torsion spring, and in that the hose means is twisted with a closed valve.

4. A catheter valve according to claim 2, characterized in that the sleeve is a sliding sleeve and the spring a coil spring, and in that the hose means is kinked with a closed valve.

5. A catheter valve according to claim 1, characterized in that the hose means closed by kinking is opened by axial displacement of said spring-loaded element.

6. A catheter valve according to claim 5, characterized in that the valve includes means securing the sleeve against rotary movements.

7. A catheter valve according to claim 1, characterized in that the means closed by twisting is by rotary movement of said spring-loaded element.

8. A catheter valve according to claim 7, characterized in that the valve includes means securing the sleeve against sliding movements.

9. A catheter valve according to claim 1, characterized in that the hose means provided with a bore includes a special kinking or twisting portion which has a smaller wall thickness at its ends than in the center, the bore being substantially cylindrical and the outer surface increasing at least approximately conically from both ends.

10. A catheter valve according to claim 9, characterized in that the valve hose means is connected both with the fixed part as also with the movable element.

11. A catheter valve according to claim 10, characterized in that the fixed part is provided with a support portion for the hand opening the valve.

12. A catheter valve according to claim 1, characterized in that the relatively fixed part is provided with a support portion for the hand opening the valve.

13. A normally closed catheter valve adapted to be connected to the end of a catheter tube and operable to be temporarily opened during actuation thereof, comprising two relatively movable valve elements arranged substantially coaxially to one another and defining therebetween a space, one of said elements being provided with a bore therethrough, a valve hose means located within said space, said valve hose means being connected with its one end to said one element substantially in extension of said bore and being operatively associated near its other end with the other of said two elements, said valve hose means leading to a discharge at the other end thereof and being closed in the normal non-actuated position of the catheter valve by deformation of the hose means, and means including spring means operatively connected with said two valve elements for normally urging the same into their normal position in which the catheter valve is closed by deformation of the hose means, while enabling temporary opening of the catheter valve by relative movement of said two elements which are automatically returned to the normally closed valve condition by the action of the spring means when released.

14. A catheter valve according to claim 13, wherein said valve hose means has a wall thickness in its center area which is different from the thickness in the end areas thereof to facilitate deformation of the hose means into the closed position thereof.

15. A catheter valve according to claim 13, characterized in that the valve hose means is closed by at least a single kink.

16. A catheter valve according to claim 13, characterized in that said valve hose means is closed by at least one fold of the hose means.

17. A catheter valve according to claim 13, characterized in that the valve hose means is closed by at least one twist.

18. A catheter valve according to claim 13, characterized in that the hose means provided with a bore includes a special kinking or twisting portion which has a smaller wall thickness at its ends than in the center, the bore being substantially cylindrical and the outer surface increasing at least approximately conically from both ends.

19. A catheter valve according to claim 1, wherein the hose means includes a special kinking or twisting portion which has a different wall thickness at its ends than in the center.

20. A normally closed catheter valve adapted to be connected to the end of a catheter hose, comprising two substantially coaxially arranged valve elements operable to telescope one within the other and defining therebetween a space, a valve hose means on the inside of said catheter valve, one of said elements being provided with a bore, said valve hose means, which is located within said space, being connected to said one element and being operatively associated with the other element, said valve hose means being closed in the normal non-actuated position of the catheter valve by deformation of the hose means and being open upon actuation of the valve, and spring means normally urging said two elements into their relative position in which said space is reduced and the hose means is deformed to close the catheter valve.

21. A normally closed catheter valve operable to be opened by actuation thereof comprising a relatively fixed part with a through-flow bore, a rubber elastic valve hose means on the inside of the valve and adjoining the relatively fixed part substantially in extension of said bore, said valve hose means being closed in the non-actuated normal position of the valve by deformation of the hose means and being continuously open while the valve is actuated, a spring-loaded element, a spring operatively connected with said spring-loaded element, said spring-loaded element being operatively associated with said valve hose means and being movable relative to the relatively fixed part in the axial direction of said bore and operable by its movement in a direction opposite the spring force to open the closed hose means.

22. A catheter valve according to claim 21, wherein the hose means includes a special kinking portion which has a different wall thickness at its ends than in the center.

* * * * *